BLORE, KLARQUIST, SPARKMAN,
CAMPBELL AND LEIGH
Do. No. 17058 Sheet 2/2
Inventor: ELWIN REASC
April 9, 1974 E. REASONER Plant Pat. 3,539
ROSE PLANT
Filed Dec. 21, 1972
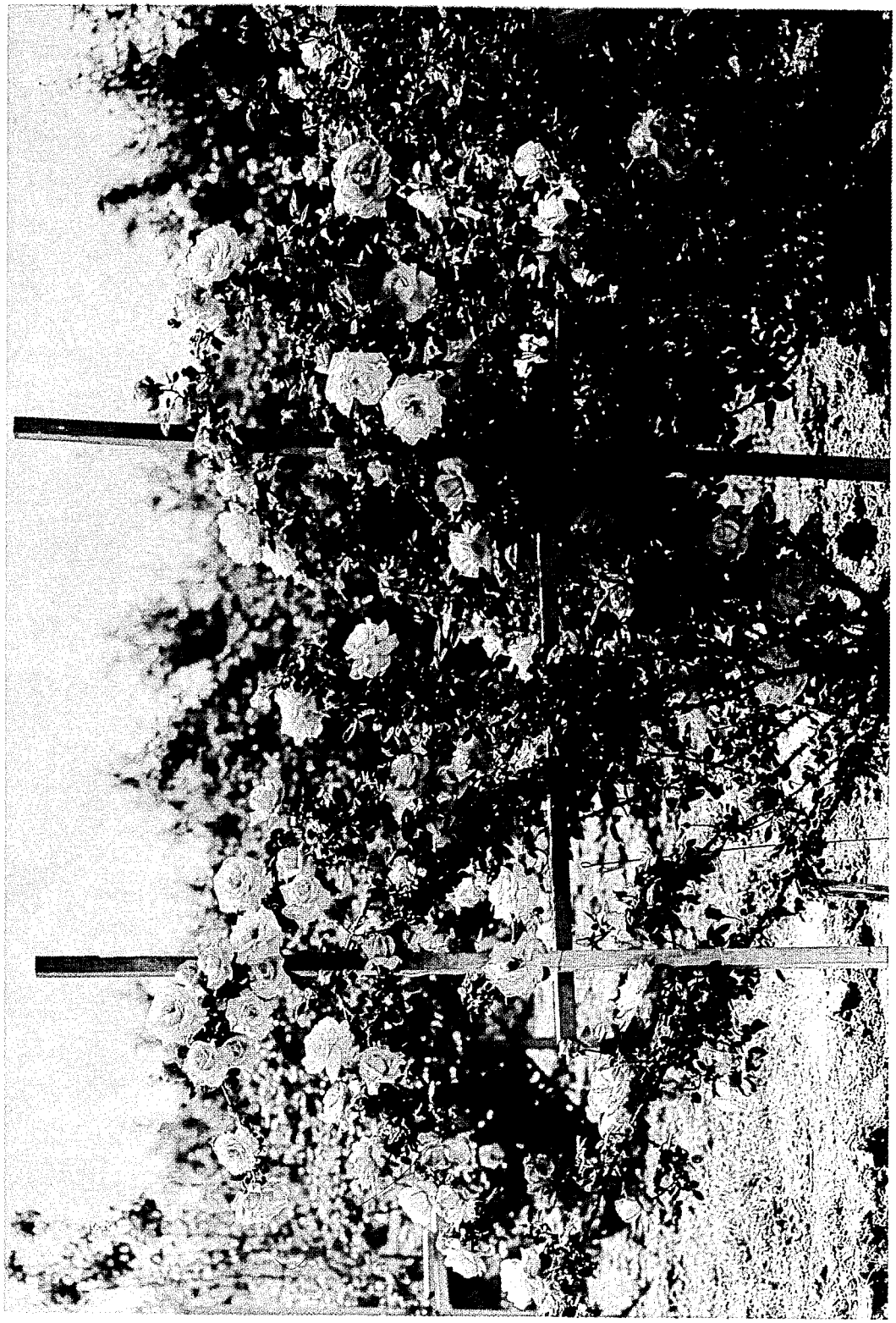

United States Patent Office

Plant Pat. 3,539
Patented Apr. 9, 1974

3,539
ROSE PLANT

Elwin Reasoner, Wasco, Calif., assignor to Jackson & Perkins Company, Medford, Oreg.

Filed Dec. 21, 1972, Ser. No. 317,181
Int. Cl. A01h 5/00
U.S. Cl. Plt.—5 1 Claim The present invention relates to a new and distinct variety of rose plant of the climber class, which was discovered by me as a sport of the variety First Prize, U.S. Plant Pat. No. 2,774.

At the time of my discovery aforementioned, I was in charge of the growing of a large block of plants of the bush rose variety, First Prize being grown in fields at Wasco, Calif.

In the course of one of my inspections of these fields, my attention was attracted to one plane on which appeared a climbing branch. Upon close examination of this plant, I found that it had sported and I thereupon promptly took steps to preserve the sport, keep it under observation, and to asexually reproduce the same by budding, as performed at Wasco, Calif. for the purpose of determining whether its climbing habit was fixed and transmissible by asexual reproductions. The climbing habit was fully confirmed and transmitted through several propagations.

The parent variety First Prize is a popular rose variety of the bush type, hybrid tea class, but so far as I am aware, it has never previously exhibited a climbing habit and its growth has been that of the average bush rose.

The new variety is substantially identical in all respects to its parent, except that it is definitely a climber, as evidenced by its long, strong canes which attain a mature length of at least ten feet or more. In view of the general similarities between the new sport variety and its parent, except as noted in the foregoing, it is unnecessary specifically to describe the new variety in detail herein, since it otherwise substantially conforms to the detailed description embodied in Plant Pat. 2,774 (issued Aug. 22, 1967, to which reference may be readily had).

The accompanying illustration shows a typical specimen of my new variety showing the climbing habit of growth, the colors of various vegetative parts being as nearly true as it is reasonably possible to make the same in a color illustration of this character.

I claim:

1. A new and distinct variety of rose plant of the climber class, substantially as herein shown and described, characterized particularly as to novelty by being substantially identical with its parent variety, First Prize, U.S. Plant Pat. 2,774 in almost every respect, but being distinguished therefrom by its long, strong canes which attain a mature height of at least ten feet or more, indicative of its climbing habit of growth.

No references cited.

ROBERT E. BAGWILL, Primary Examiner